(12) United States Patent  
MacKinnon

(10) Patent No.: US 9,138,140 B2
(45) Date of Patent: Sep. 22, 2015

(54) COMPACT IRIS IMAGING SYSTEM

(75) Inventor: Neil MacKinnon, San Jose, CA (US)

(73) Assignee: LRS Identity, Inc., San Mateo, CA (US)

( * ) Notice: Subject to any disclaimer, the term of this patent is extended or adjusted under 35 U.S.C. 154(b) by 548 days.

(21) Appl. No.: 13/424,633

(22) Filed: Mar. 20, 2012

(65) Prior Publication Data

US 2013/0250085 A1 Sep. 26, 2013

(51) Int. Cl.
*H04N 9/47* (2006.01)
*H04N 7/18* (2006.01)
*A61B 3/12* (2006.01)
*H04N 5/225* (2006.01)
*G06K 9/00* (2006.01)
*G06K 9/20* (2006.01)

(52) U.S. Cl.
CPC .......... *A61B 3/1216* (2013.01); *G06K 9/00604* (2013.01); *G06K 9/2036* (2013.01); *H04N 5/2256* (2013.01)

(58) Field of Classification Search
CPC ............................ A61B 3/113; G06K 9/00604
USPC ........................................................ 348/78
See application file for complete search history.

(56) References Cited

U.S. PATENT DOCUMENTS

| 5,016,282 A | 5/1991 | Tomono et al. |
| 2002/0164054 A1* | 11/2002 | McCartney et al. .......... 382/118 |
| 2010/0278394 A1* | 11/2010 | Raguin et al. ................. 382/117 |
| 2011/0285836 A1 | 11/2011 | Friedman et al. |

OTHER PUBLICATIONS

Dodgson, N.A., "Variation and Extrema of Human Interpupillary Distance," Stereoscopic Displays and Virtual Reality Systems XI, Woods, A.J. et al., eds., Proc. of SPIE, 2004, pp. 36-46, vol. 5291.
PCT International Search Report and Written Opinion, PCT Application No. PCT/US2013/028643, May 9, 2013, ten pages.

* cited by examiner

*Primary Examiner* — Chikaodili E Anyikire
(74) *Attorney, Agent, or Firm* — Fenwick & West LLP

(57) ABSTRACT

An iris imaging and illumination system is used to resolve and record the fine musculature features of an iris. The system can improve the quality of an iris image and facilitate the image capturing process by focusing illumination on an ocular area of a subject. By limiting illumination of other parts of a face, reflections from the face are reduced. The system has a compact physical arrangement by placing the illumination sources proximate to one another and splaying them in order to focus illumination on the ocular areas of a subject.

18 Claims, 4 Drawing Sheets

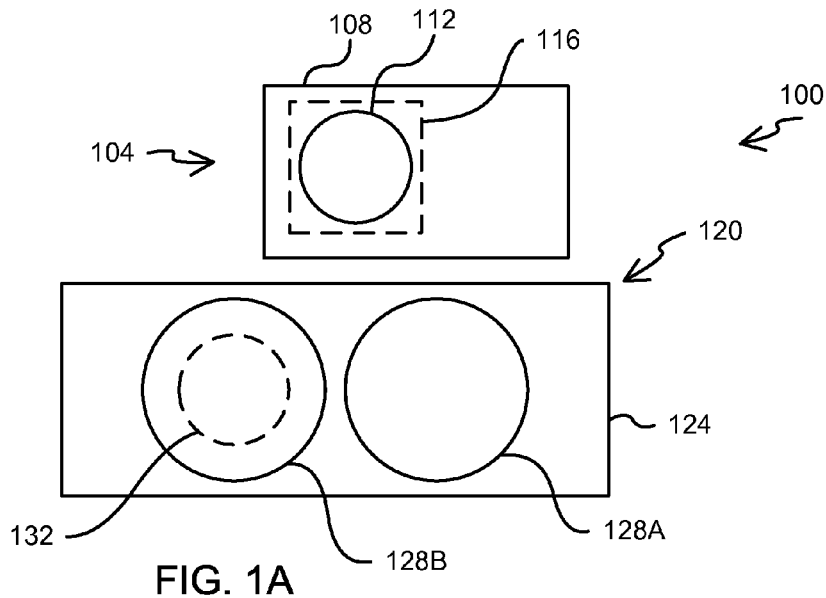
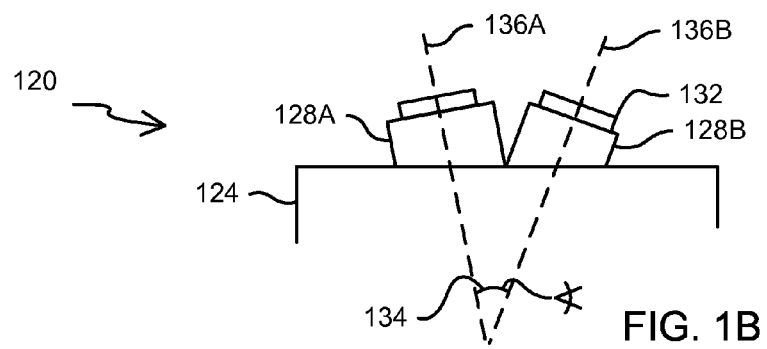
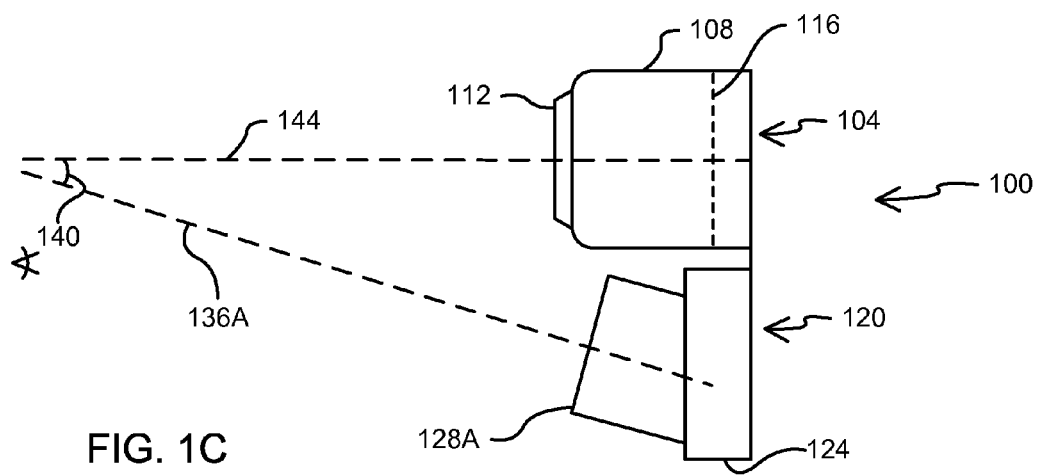

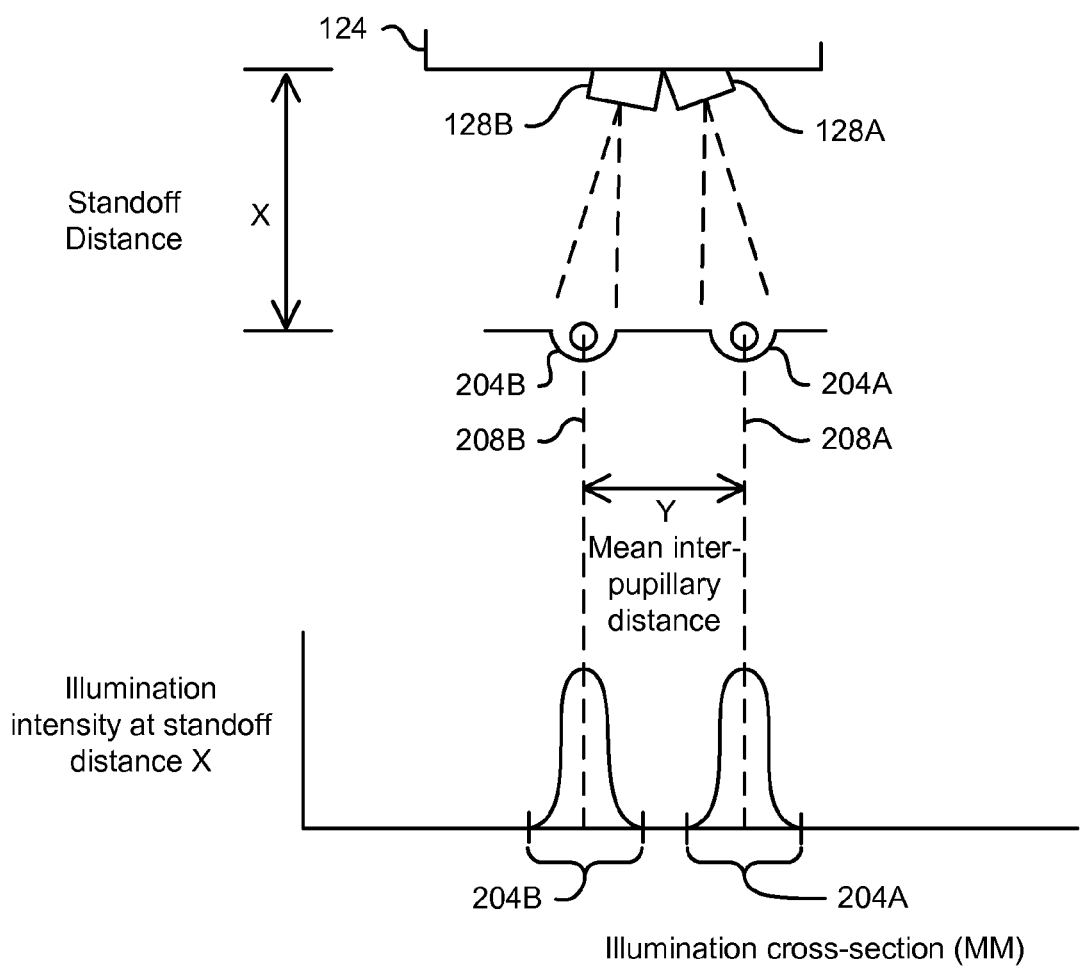

COMPACT IRIS IMAGING SYSTEM

BACKGROUND

1. Technical Field

The present disclosure relates to imaging of an iris. Specifically, the present disclosure relates to a compact iris imaging apparatus used to capture an image of an iris at a standoff distance.

2. Description of Related Art

Imaging of an iris is often performed by illuminating a spatial volume that includes the face of a subject and then recording an image of an illuminated iris or irises. Infra-red light is often used for illumination because pigmentation in the iris is more transparent in the infra-red spectrum. The transparency of the pigmentation exposes the fine structures of the iris to the imaging system. The resulting image can be used for, as an example, biometric identification. Iris-based biometric identification typically requires a spatial resolution of 200 microns, or better, with a pixel resolution of approximately 60 microns for an ISO standard 19794-6-compliant image. In general higher spatial resolution leads to better matching performance by distinguishing the fine muscle structure of human irises.

Illumination systems used for iris imaging, particularly biometric imaging, regularly comprise multiple illumination sources that flood the capture volume (i.e., the volume in space over which the iris imaging system captures images) with a uniform or near uniform intensity of light. This type of arrangement facilitates adequate illumination of the capture volume and any irises within the capture volume.

SUMMARY

In one embodiment, the iris imaging system of the present disclosure includes an iris imaging sub-assembly and an iris illumination sub-assembly. The iris imaging sub-assembly includes an optical lens having a focal plane with a sensor substantially disposed in the focal plane of the optical lens. The sensor has an imaging axis that is substantially perpendicular to the focal plane of the lens. The sensor is configured to capture an image of an iris of a subject at a standoff distance of at least 100 mm. The iris illumination sub-assembly includes a first illumination source that is configured to illuminate a first ocular area of the subject, and a second illumination source that is configured to illuminate a second ocular area of the subject. The first and the second illumination sources produce a dual-lobed irradiance distribution. Furthermore, a center point of the first lobe and a center point of the second lobe are separated approximately by an interpupillary distance at a standoff distance. Thus, the iris imaging system of the present disclosure can focus illumination on the ocular areas of the subject, and the irises therein, in a way that minimizes light reflection from other parts of the subject's face. This, in turn, enables the iris imaging system to capture images of the subject's irises, while also enabling a physically compact arrangement of the system.

BRIEF DESCRIPTION OF THE DRAWINGS

FIG. 1A is a schematic illustration of a frontal view of an iris imaging system according to an embodiment of the present disclosure, wherein the system includes both an iris imaging sub-assembly and an iris illumination sub-assembly.

FIG. 1B is a plan view schematic illustration of an embodiment of the iris imaging system depicted in FIG. 1A wherein two illumination sources are splayed apart at an angle.

FIG. 1C is a side view schematic illustration of the iris imaging system depicted in FIGS. 1A and 1B, wherein an angle of tilt of an illumination source toward the iris imaging sub-assembly is shown.

FIG. 2A is a schematic plan view illustration of the illumination volumes associated with each illumination source in relation to the eyes of a subject, wherein the subject is at a standoff distance X, in accordance with an embodiment.

FIG. 2B is a graph of the illumination intensity at the standoff distance of the subject as a function of an interpupillary distance, in accordance with an embodiment.

Figure 3A:
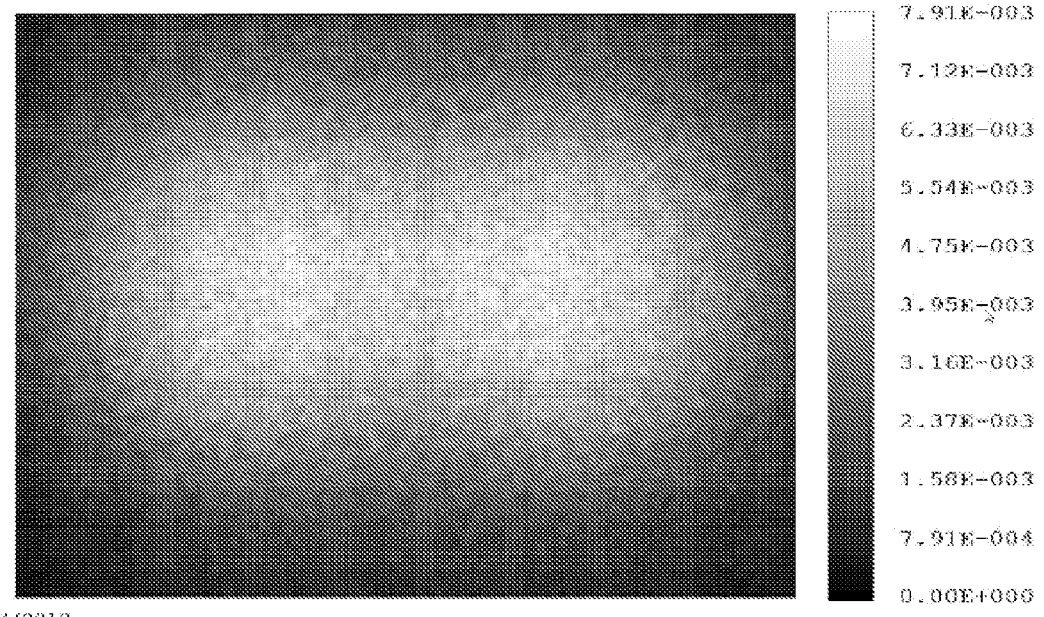
FIG. 3A is a simulation of the illumination intensity produced by the iris illumination sub-assembly of the iris imaging system at the standoff distance, in accordance with an embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

The present disclosure describes exemplary embodiments of an iris imaging system that has a physically compact arrangement using an illumination source arrangement that primarily illuminates the ocular areas (i.e., areas including and surrounding the eyes that are approximately defined by the bones forming the eye sockets) of a subject's face at a standoff distance. This provides illumination to resolve and record an image of an iris of the subject. This image can be used, for example, in biometric identification of the subject. The image of a subject's iris is obtained by illuminating primarily the ocular areas of the subject, and limiting the amount of light illuminating other portions of the subject's face. This limited illumination reduces reflections from the face of the subject that can direct undesired light toward the iris imaging system, thereby degrading the quality of the iris image.

Furthermore, exemplary systems of the present disclosure have a compact form created by, for example, positioning two illumination sources proximate to one another and splaying them, thereby primarily directing the illumination from each source to a corresponding ocular area on the face of the subject at a standoff distance. This compact arrangement can be used to produce a device that can be held in one hand while using the device to biometrically identify a subject. As used herein, the standoff distance is the distance separating the iris imaging system and the iris (or irises) of the subject to be imaged. The illumination pattern can be set for one or more standoff distances, by, for example, adjusting the angle of splay between the two illumination sources based on a selected standoff distance and an average interpupillary distance. At the standoff distance, the approximate centers of the illumination areas are separated approximately by an interpupillary distance.

Iris Imaging System Embodiments

FIG. 1A is a schematic, front-view illustration of one embodiment of an iris imaging system 100 of the present disclosure. The imaging system 100 includes an imaging sub-assembly 104 and an illuminator sub-assembly 120 that optionally can be connected together. The imaging sub-assembly 104 includes an imager body 108, an optical lens 112, and a sensor 116.

The imager body 108 of the imaging sub-assembly 104 provides a structure onto which the optical lens 112 attaches, and within which the sensor 116 resides. Furthermore, the imager body 108 excludes undesired or stray light from being detected by the sensor 116, thereby improving the quality of an image captured by the sensor 116. Excluding undesired light may also improve the performance of the sensor 116 and the performance of any image processors or computer-executable code used to refine the image (not shown) in communication with the sensor 116.

The optical lens 112 is configured to receive an image of one or more irises disposed within the capture volume at approximately the standoff distance. The optical lens 112 then projects the image onto the sensor 116. The standoff distance is illustrated in FIG. 2A and is explained in more detail below in the context of that figure. As will be appreciated, the sensor 116 is substantially disposed in the focal plane of the optical lens 112 and has an imaging axis substantially perpendicular to the focal plane of the optical lens, thereby enabling a focused image of the iris to be received by the sensor 116. The sensor 116 communicates the image to a processor (not shown) for example, to record the image of the iris in a computer-readable medium, process the image, or biometrically identify the subject of the iris imaging. It will be appreciated that additional imaging-related tasks can be performed by a processor on the image of the iris that is captured by the sensor 116.

The illuminator sub-assembly 120 includes an illuminator body 124, a first illumination source 128A and a second illumination source 128B. The illuminator sub-assembly 120 may also optionally include one or more of an illumination lens 132. The first and the second illumination sources 128A and 128B are positioned proximate to one another and are connected to the illuminator body 124. In some embodiments, the first and the second illumination sources 128A and 128B are positioned apart approximately by an interpupillary distance. In other embodiments, the first and the second illumination sources 128A and 128B are placed approximately adjacent to one another with their separation limited only by the diameter of the sources themselves, their associated structures or operating circuitry, and/or filters, lenses, and/or other attachments used in conjunction with the illumination sources. Other example arrangements of the first and the second illumination sources 128A and 128B are discussed in more detail below in the context of FIGS. 1B and 1C. Regardless of the arrangement, the first and the second illumination sources 128A and 128B produce a dual-lobed irradiance or illumination distribution, wherein the lobes of the distribution are located approximately at the ocular areas of a subject separated from the illumination sources by approximately the standoff distance. The distribution of light at the ocular areas will be discussed in more detail below in the context of FIGS. 2A, 2B, and 3.

It will be appreciated that the system 100 need not be limited to the illumination sources 128A and 128B. In other embodiments, a single illumination source may be used, in connection with a lens, to produce a dual-lobed irradiance distribution used to illuminate ocular areas of a subject at a standoff distance. In further embodiments, a third and a fourth illumination source may be attached to the system 100 and configured to illuminate an ocular area of a subject at a second standoff distance different from the first standoff distance. As described above, the third and fourth illumination sources can produce a dual-lobed irradiance distribution at the second standoff distance, wherein a center point of a third lobe and a center point of a fourth lobe are separated approximately by an interpupillary distance at the second standoff distance. For ease of description, the embodiment having two illumination sources will be described as an example below.

As mentioned above, the illumination sources 128A and 128B produce illumination in the infra-red region of the light spectrum in order to better resolve the fine musculature structures of the iris. In some examples, this infra-red illumination includes wavelengths of light from approximately 700 nm to approximately 900 nm, although those skilled in the art will appreciate that other wavelengths can be used. In some embodiments, the illumination sources 128A and 128B are semiconductor illumination devices, such as light emitting diodes ("LEDs"), that can be individual devices or a group of two or more semiconductor illumination devices. In other examples, thermal illumination devices, such as electrically resistant filaments, can be used to produce illumination of the desired wavelength. In yet further examples, filters can be used to further narrow the wavelength of light emitted by the illumination sources 128A and 128B. In still further examples, filters can be used to further narrow the wavelength of light emitted by the illumination sources in order to increase the spectral brightness of the illumination that is applied to the subject. This can allow for more efficient discrimination of extraneous background images from the iris image.

Figure 3B:
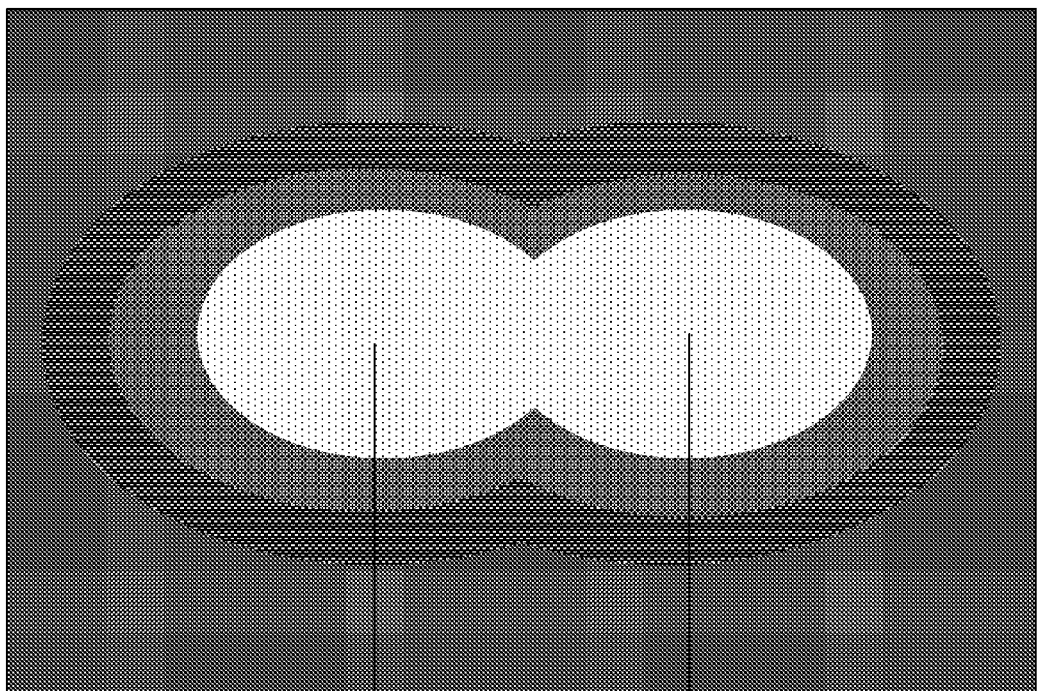
FIG. 3B is a schematic representation illustrating the dual-lobed irradiance distribution.

In addition to the optional filters mentioned above, the illumination lens 132 may also be used with one or both of the illumination sources 128A and 128B in order to further focus, defocus, or otherwise direct light from the illumination sources to the ocular areas of a subject. The illumination lens 132 may be used with one or both of illumination sources 128A and 128B and may be used to tailor the shape and/or intensity of the light distribution at the standoff distance. For example, two illumination lenses 132 may be used for focusing illumination from the first illumination source and the second illumination source at the ocular areas, wherein the first illumination lens and the second illumination lens are configured to produce a dual-lobed irradiance distribution, as schematically illustrated in FIGS. 2B, 3A, and 3B. In other examples, a single illumination lens 132 can be used to produce a dual-lobed irradiance distribution from a single illumination source (e.g., 128A). In still other examples, the irradiance distribution need not be approximately circularly symmetric, as shown in the figures. That is, asymmetric irradiance distributions having non-symmetric aspect rations can be achieved using, for example, lenses that focus illumination toward the iris and away from other parts of the ocular areas. The illumination lens 132 can be used to filter the light distribution in cases where illumination sources 128A and 128B are unable to perform the filtering. The methods used to design and fabricate the illumination lens 132 are well known in the art.

In one embodiment of the iris imaging system 100, the imager body 108 can be connected to the illuminator body 124, either directly or indirectly so that the two sub-assemblies 104 and 120 can be operated as a single unit. In other examples, the iris imaging system 100 and its various sub-assemblies and components are arranged so that the system 100 is operated as a hand-held system. As will be described in more detail below, one example of this embodiment includes the illumination sources 128A and 128B immediately adjacent and splayed at an angle of between 3° and 6°. This arrangement enables the physically compact system 100 while still enabling the illumination from the illumination sources 128A and 128B to be directed approximately to the ocular areas of the subject at the standoff distance.

FIG. 1B is a schematic, plan-view illustration of one embodiment of the illuminator sub-assembly 120. In this embodiment, the physical compactness of the system 100 is facilitated by using some or all of the embodiments discussed above. That is, the illumination sources 128A and 128B are placed in contact with another, thereby reducing their contribution to the size of the illuminator sub-assembly 120. The illumination sources 128A and 128B are then splayed apart by an illuminator angle 134 of between approximately 3° to approximately 6° as defined by illumination axes 136A and 136B. This angle facilitates the direction of illumination to the ocular areas of the subject, thereby forming the dual-lobed irradiance distribution described above, while also facilitating the compact arrangement of the system 100. Those skilled in the art will appreciate that the illuminator angle 134 can be changed as a function of the standoff distance in order to direct illumination to the ocular areas of a subject.

FIG. 1C is a schematic, side-view depiction of one embodiment of the iris imaging system 100 of the present disclosure, in which an offset angle 140 is shown. The offset angle 140 separates an imaging axis 144 from the illumination axes 136A (shown) and/or 136B (not shown). One reason for such an offset is that the contrast between the pupil and the iris in an image can be degraded by the presence of a retinal retro-reflection to such an extent that image processing software cannot reliably segment the image in an automated fashion. The effect, commonly known as red-eye, can occur when an imaging axis, (e.g., the imaging axis 144), and an illumination axis, (e.g., the illumination axis 136A), are not separated by a large enough angle. The offset angle 140 is created in this embodiment by tilting the illumination sources 128A and 128B toward the imager body 108. In this embodiment, the offset angle 140 is approximately 7°, but it will be appreciated that red-eye can be prevented using any of a variety offset angles to separate the imaging axis 144 from that of the illumination axis 136A.

Furthermore, upon reading this disclosure, those skilled in the art will appreciate that other arrangements of the components of system 100 may accomplish the effects described above without departing from the teachings herein. For illustration, the illuminator body 124 can be mounted above, below, or on a side of the imager body 108. In any such embodiment, the relative orientation of the illuminator body 124 and the imager body 108 can be established to produce the offset angle 140, thereby preventing the retinal retro-reflection.

Light Distribution

FIGS. 2A and 2B illustrate distribution of light projected from the illumination sources 128A and 128B onto ocular areas 204A and 204B of a subject located at a standoff distance X. Specifically, FIG. 2A shows an approximation of the light path from each of the illumination sources 128A and 128B, whereas FIG. 2B illustrates an example of a light irradiance distribution on the face of a subject originating from the illumination sources.

Turning first to FIG. 2A, the illumination sources 128A and 128B, housed by the illuminator body 124, direct illumination to a capture volume containing the ocular areas 204A and 204B of a subject, thereby illuminating the irises disposed therein. While the scenario illustrated in FIG. 2A shows the light rays originating at the illumination sources 128A and 128B and diverging as the light approaches the ocular areas 204A and 204B, this need not necessarily be the case. As known to those skilled in the art, the illumination sources 128A and 128B, with or without the illumination lenses 138A and 138B, can also cause light to converge toward the ocular areas 204A and 204B, or even cause the light to converge to a focal point between the illumination sources 128A and 128B and the standoff distance X, before diverging to illuminate the ocular areas at the standoff distance.

As described above, the standoff distance X shown in FIG. 2A is a function of the capture volume of system 100, the resolution of the sensor 116, the illumination intensity and area of irradiance produced by the illumination sources 128A and 128B, and optionally the illumination lenses 138A and 138B, as well as other factors. In one embodiment, the system 100 is configured using some or all of the features described above such that the standoff distance X is greater than 100 mm. In another embodiment, the system 100 is configured such that the standoff distance X is between 100 mm and 1000 mm. In yet another embodiment, the system 100 is configured such that the standoff distance X is between 250 mm and 300 mm. In still another embodiment, the illumination (whether a flash or a longer duration), is optimized based on a measured distance to the subject. In this embodiment, the illumination, from one or more illumination sources, can also be optimized to maximize the illumination based on both the power and standoff distance.

FIG. 2B depicts the irradiance distribution on the face of the subject at the standoff distance X. As shown, the irradiance distribution within each ocular area 204A and 204B is an approximately Gaussian distribution that is centered approximately at the iris locations 208A and 208B. The irradiance distribution need not be Gaussian, but rather need only illuminate either or both of ocular areas 204A and 204B and irises 208A or 208B, as described above. As is also shown, the irises at iris locations 208A and 208B are separated by an interpupillary distance Y, which also coincides with the maxima of the irradiance distributions in this example. The mean interpupillary distance Y is typically between 60 mm and 65 mm, although the interpupillary distance of individuals can range from about 40 mm to about 80 mm, as explained in the literature by Dodgson (*Variation and Extrema of Human Interpupillary Distance*, Proc. SPIE, Vol. 5291m pp. 36-34).

FIG. 3A depicts a simulation showing a plan view of an irradiance distribution according to the present disclosure. The features of this simulation, such as the dual-lobed nature of the intensity distribution, are schematically illustrated in FIG. 3B for clarity.

FIG. 3B is a schematic illustration of the dual-lobed irradiance distribution. As illustrated, the maximum of each distribution is approximately centered at the iris locations 208A and 208B. As discussed above, these maxima are separated by a mean interpupillary distance Y. While this figure includes distinct boundaries between irradiance intensity levels, it will be appreciated that these boundaries are an artifact of the illustration.

Additional Configuration Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure. The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based herein. Accordingly, the disclosure of the embodiments of the invention is intended to be illustrative, but not limiting, of the scope of the invention, which is set forth in the following claims.

What is claimed is:

1. An iris imaging system comprising:
   an iris imaging sub-assembly, comprising:
      an optical lens having a focal plane; and
      a sensor substantially disposed in the focal plane of the optical lens, the sensor having an imaging axis substantially perpendicular to the focal plane, wherein the sensor is configured to capture an image of an iris of a subject at a standoff distance of at least 100 mm; and
   an iris illumination sub-assembly connected to the iris imaging sub-assembly, the iris illumination sub-assembly comprising:
      a first illumination source configured to illuminate a first ocular area of the subject;
      a second illumination source configured to illuminate a second ocular area of the subject; and
      wherein the illumination sources produce a dual-lobed irradiance distribution, and further wherein a center point of a first lobe and a center point of a second lobe are separated approximately by an interpupillary distance at the standoff distance.

2. The iris imaging system of claim 1, wherein the first illumination source and the second illumination source are splayed by between approximately 3° and approximately 6°.

3. The iris imaging system of claim 1, wherein the first illumination source and the second illumination source are tilted in the direction of the optical lens by approximately 7°.

4. The iris imaging system of claim 1, wherein the standoff distance is between approximately 100 mm and approximately 1000 mm.

5. The iris imaging system of claim 4, wherein the standoff distance is between approximately 200 mm and approximately 400 mm.

6. The iris imaging system of claim 5, wherein the standoff distance is between approximately 250 mm and approximately 300 mm.

7. The iris imaging system of claim 1, further comprising a first illumination lens and a second illumination lens focusing illumination from the first illumination source and the second illumination source at the ocular areas, wherein the first illumination lens and the second illumination lens are configured to produce a dual-lobed irradiance distribution.

8. The iris imaging system of claim 1, wherein the first and the second illumination sources produce infra-red illumination.

9. The iris imaging system of claim 8, wherein the infra-red illumination has wavelengths from approximately 700 nm to approximately 900 nm.

10. The iris imaging system of claim 1, wherein the first and second illumination sources are semiconductor illumination devices.

11. The iris imaging system of claim 10, wherein the semiconductor illumination devices each include a group of two or more semiconductor illumination devices.

12. The iris imaging system of claim 2, wherein the interpupillary distance is from approximately 40 mm to approximately 80 mm.

13. The iris imaging system of claim 12, wherein the interpupillary distance is from approximately 60 mm to approximately 65 mm.

14. The iris imaging system of claim 1, further comprising a third and a fourth illumination source configured to illuminate an ocular area of a subject at a second standoff distance different from the first standoff distance, wherein the third and fourth illumination sources produce a dual-lobed irradiance distribution at the second standoff distance, and further wherein a center point of a third lobe and a center point of a fourth lobe are separated approximately by an interpupillary distance at the second standoff distance.

15. An iris imaging system comprising:
   an iris imaging sub-assembly, comprising:
      an optical lens having a focal plane; and
      a sensor substantially disposed in the focal plane of the optical lens, the sensor having an imaging axis substantially perpendicular to the focal plane, wherein the sensor is configured to capture an image of an iris of a subject at a standoff distance of at least 100 mm; and
   an iris illumination sub-assembly connected to the iris imaging sub-assembly, the iris illumination sub-assembly comprising:
      an illumination source configured to illuminate a first ocular area and a second ocular area of the subject; and
      wherein the illumination source produces a dual-lobed irradiance distribution, and further wherein a center point of a first lobe and a center point of a second lobe are separated approximately by an interpupillary distance at the standoff distance.

16. The iris imaging system of claim 15, further comprising an illumination lens for focusing illumination from the illumination source at the ocular areas of the subject, wherein the illumination lens is configured to produce a dual-lobed irradiance distribution.

17. The imaging system of claim 15, wherein the standoff distance is between approximately 100 mm and approximately 1000 mm.

18. The iris imaging system of claim 15, wherein the illumination source is tilted in the direction of the optical lens by approximately 7°.

* * * * *